United States Patent [19]

French et al.

[11] Patent Number: 5,463,035
[45] Date of Patent: Oct. 31, 1995

[54] PROCESS FOR PURIFYING PENTOSTATIN

[75] Inventors: James C. French, Ann Arbor, Mich.; Colin R. Edmunds, Abergavenny; Peter McDonnell, Caerleon Gwent, both of United Kingdom; Howard D. H. Showalter, Ann Arbor, Mich.

[73] Assignee: Warner-Lambert Company, Morris Plains, N.J.

[21] Appl. No.: 396,443

[22] Filed: Feb. 28, 1995

Related U.S. Application Data

[63] Continuation of Ser. No. 224,392, Apr. 7, 1994, abandoned, which is a continuation of Ser. No. 738,715, Jul. 31, 1991, abandoned.

[51] Int. Cl.$^6$ ............................ C07H 19/23; C07H 19/04
[52] U.S. Cl. ............................ 536/55.3; 536/27.2; 435/87
[58] Field of Search ............................ 536/26.73, 55.3, 536/27.2; 435/87

[56] References Cited

U.S. PATENT DOCUMENTS 3,923,785  12/1975  Ryder et al. .................... 260/211.5
4,713,372  12/1987  Schaumberg et al. ............ 514/45
4,908,441  3/1990  Cook et al. ........................ 536/27

FOREIGN PATENT DOCUMENTS 0207017  8/1988  European Pat. Off. .

OTHER PUBLICATIONS

PCT Search Report, PCT/US92/05946.
*Analytical Biochemistry*, vol. 55, Cory et al., pp. 449–456 (1973).
*J. Steroid Biochem.*, vol. 18, No. 3, Fotsis et al., pp. 357–363 (1983).

*Primary Examiner*—Douglas W. Robinson
*Assistant Examiner*—Gary L. Kunz
*Attorney, Agent, or Firm*—Todd M. Crissey

[57] ABSTRACT

A process for purifying pentostatin from a crude fermentation beer comprising the steps of 1) applying the fermentation beer to a strong cation exchange resin; 2) eluting with ammonium hydroxide; 3) concentrating the eluate; 4) applying the concentrated eluate to a strongly basic anion exchange resin charged with borate ion; 5) eluting with water; 6) applying this eluate to styrene-divinylbenzene beads prewashed with ethanol; 7) eluting the beads with water; and 8) recryslliyzing the pentostatin from water and methanol to yield a product that is greater than 99.7% pure.

6 Claims, No Drawings

PROCESS FOR PURIFYING PENTOSTATIN

This is a continuation of application Ser. No. 08/224,392 filed Apr. 7, 1994, now abandoned, which is a continuation of Ser. No. 07/738,715 filed Jul. 31, 1991, now abandoned.

BACKGROUND OF THE INVENTION

Pentostatin is (R)-3-(2-deoxy-β-D-erythropentofuranosyl) -3,6,7,8-tetrahydroimidazo [4,5-d]-[1,3] diazepin-8-ol having the structure:

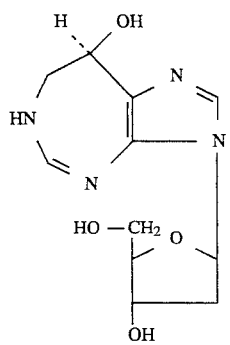

It is a potent adenosine deaminase inhibitor and is useful as an antileukemic agent. U.S. Pat. No. 3,923,785, issued Dec. 2, 1975, describes the production of pentostatin by fermentation of a strain of *Streptomyces antibioticus* which is on deposit as NRRL 3238. U.S. Pat. No. 3,923,785 also describes the isolation and purification of pentostatin from the fermentation beer.

The present invention provides a markedly improved procedure for the isolation and purification of pentostatin. The present invention utilizes a combination of ion exchange resins and SEPABEADS 207 which has proven to increase dramatically the amount of pure compound recovered from the fermentation broth. Without this improved recovery process the commercialization of pentostatin would be impractical due to the high cost of production of the compound in pure form.

SUMMARY OF THE INVENTION

The present invention provides a novel process for isolating pentostatin. More particularly, the present invention provides a process for chromatographically isolating pentostatin from a crude concentrate which comprises applying the concentrate to a strongly basic borate anion exchange resin followed by application to an activated bed of SEPABEADS SP207, or the equivalent thereof, and collection of the fractions containing pentostatin.

DETAILED DESCRIPTION OF THE INVENTION

As set forth above the fermentation process for producing pentostatin is described in U.S. Pat. No. 3,923,785, which patent is incorporated herein by reference.

The crude fermentation concentrate is obtained by retaining pentostatin from the fermentation beer on a strong cation exchange resin followed by elution with ammonium hydroxide and concentration of the eluate to a volume approximately 1/200 of the starting beer volume. This concentrate, which contains several known contaminants including the "S" isomer (the C-8 epimer) of pentostatin, coformycin, 2'-deoxyguanosine, vidarabine, and cytosine, is then processed in 3 phases: 1) a precipitation step to remove gross impurities, 2) chromatography using a strongly basic anion exchange resin in the borate form and then SEPABEADS SP207, or the equivalent thereof, and 3) crystallization. In particular, it is the chromatographic phase that gives rise to the present invention. It has been found that the use of a strongly basic anion exchange resin in combination with SEPABEADS (Trademark of Mitsubishi) SP207 gives higher yields of pure product not realized heretofore. The anion exchange resins useful in the present process contain a quaternary ammonium functionality and are strongly basic anion exchange resins. There are many such resins commercially available. Typical are the ion exchange resins sold under the trademark of PUROLITE A-425 (trademark owned by the Purolite Company) and the ion exchange resins sold under the trademark of DOWEX (trademark owned by the Dow Chemical Company) series of strongly basic anion exchange resins which may be used and which comprise a styrene-divinylbenzene (S-DVB) polymeric backbone and a trimethylammonium or a dimethylethanolammonium side chain as generally depicted below:

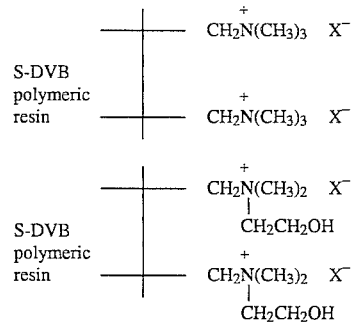

The above depicted anion exchange resins are commercially available as DOWEX-1X1, DOWEX-1X2, DOWEX-1X4, etc., and normally supplied in the chloride form where $X^-$ is $Cl^-$ or the hydroxide form where $X^-$ is $OH^-$.

A commercially available series of anion exchange resins containing a quaternary ammonium functionality sold under the trademark of AMBERLITE (trademark owned by the Rohm and Haas Company) may also be used. These resins are of two different types, one being a gel type and the other being a macroreticular type, and both are strongly basic. The literature describes the Amberlite series of resins as having quaternary ammonium groups attached to a styrenic or an acrylic type backbone.

There are many other commercially available resins that are equivalent to those described above and would be recognized readily by one skilled in the art as useful in the presently claimed process.

Generally, the anion ($X^-$) in the commercially available, strongly basic anion exchange resin is chloride. This resin can be converted to the borate form for use in the present invention by treatment with a borate salt such as potassium tetraborate. To accomplish this modification the commercially available resin can be placed in a column through which is percolated several bed volumes of an aqueous solution of potassium tetraborate, after which any excess borate can be removed by passing several volumes of deionized water through the column. After use, the resin can be regenerated by washing with dilute hydrochloric acid followed by deionized water followed by a solution of potassium tetraborate. Synthetic adsorbent resins sold under the trademark of SEPABEADS SP207 (trademark owned by the Mitsubishi Company), which are used in the presently claimed process, are depicted in the trade literature as being a styrene-divinylbenzene type of resin groups. SEPA-BEADS SP207 have an affinity for aromatic compounds. The product is generally represented as follows:

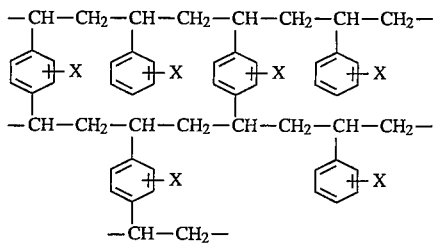

wherein the X substituent is bromine.

The following example illustrates the process of the present invention including the preparation of the initial concentrate, precipitation and the final clean-up chromatographic and crystallization phases. For all of the isolation and purification steps described below the course of each operation is monitored by assaying the several collected fractions for pentostatin content by high pressure liquid chromatography using the system:

Column: 250×4.6 mm Phenomenex, Ultremex 5 C-8 column.
Mobile Phase: 2.5 parts methanol 2.5 parts acetonitrile 95.0 parts 0.05 M aqueous $(NH_4)_2 HPO_4$ adjusted to pH 7.4 with phosphoric acid.
Flow rate: 1.0 mL per minute
Detection: 270 nm (282 nm is used for measuring the purity of the final pentostatin product)
Retention time: 10.7 minutes As is known by those skilled in analytical chromatographic procedures, the above parameters may be modified according to the nature and condition of the column used.

In the following example, Purolite A425 resin is used which is a strongly basic anion gel and is equivalent to DOWEX 1X2 with, for example, a mesh size of 100. The resin is purchased in the chloride form and is converted to the borate form as follows.

PUROLITE A425 (chloride) resin is charged to a column and converted to the borate form by percolation of 15–16 bed volumes of ca 0.7M $K_2B_4O_7$ solution. It is most convenient to dissolve the potassium tetraborate in warm (60° C.) deionized water and then cool the resulting solution to room temperature. The excess borate is rinsed from the column using deionized water (7–10 bed volumes) until a total dissolved solids meter reads 0.00 for the eluate. The column is then back washed with deionized water to remove fines and is ready for use.

In the following example the expression "bed volume" refers to the apparent volume of resin in the column after charging a suspension of new resin in water and allowing about 1 hour for settling. All subsequent references relate to this volume. PUROLITE A425 is supplied in the chloride form; conversion to the borate form, followed by rinsing and backflushing, and finally settling for one hour, leads to a bed volume increase of about 20%.

EXAMPLE

Production lots of *Streptomyces antibioticus* NRRL 3238 fermentation beer containing pentostatin are prepared according to the procedure described in U.S. Pat. No. 3,923,789, issued Dec. 2, 1975. In a typical run, 50,000 L of fermentation beer is adjusted to pH 8.5, stored at or below +15° C. for about 20 hours, and then filtered using a coated microporous filter sold under the trademark of CELITE 545. The cold filtrate is adjusted to pH 6.0 and passed through a column containing 5,000 L of DOWEX 50X4 ($NH_4^+$) that was previously conditioned with cold (about 15° C) water. The DOWEX 50 resin is then washed with water and eluted with 0.1M ammonium hydroxide followed by 0.2M ammonium hydroxide. Throughout this elution step and subsequent isolation and purification steps the course of the operation is monitored by HPLC as described above. The ammonium hydroxide eluates containing the major quantity of pentostatin are pooled and concentrated in vacuo to 250 L at a temperature less than 50° C.

Precipitation

A 50 L aliquot of the above dark, viscous concentrate is stirred with 500 L of 3A ethanol and 250 L of acetone and then allowed to stand for about 24 hours. The supernatant solution is carefully removed from a dark, tarry residue, filtered through a CELITE 50 coated filter, and concentrated in vacuo to 20 L at a temperature less than 28° C.

Chromatography

The above, darkly colored concentrate (20 L) is applied to a column containing 135 L PUROLITE A425 (borate) resin prepared as described above. Passage of the charge through the column removes a great deal of color that is retained on the resin. The resin is then eluted with 7 bed volumes of deionized water. After a forerun of about one bed volume the pH of the eluate rises abruptly and a yellow color is observed. About 90% of the pentostatin applied to the resin is eluted in the next 3 bed volumes. The pentostatin-rich fractions are pooled and applied to a column containing 120 L of Diaion SEPABEADS SP207 previously washed with aqueous ethanol followed by a thorough water wash. After all of the pentostatin charge is applied, the SEPABEAD resin is washed with 3–4 bed volumes of deionized water and then eluted with ethanol-water (10:90 w/w). After a forerun of one bed volume pentostatin begins to emerge and is essentially completely eluted in the next 2.5–3.0 bed volumes. The fractions containing the major amount of pentostatin are pooled and concentrated in vacuo to give 12 to 13% w/w solution of pentostatin. This concentrate is treated with charcoal (5% w/w with respect to pentostatin) and then filtered through CELITE 545, followed by filtration through 0.45 micron and 0.22 micron membrane filters.

Crystallizations

The final filtrate is concentrated in vacuo to a slurry containing 60% pentostatin (w/w) to which is added 10 volumes (based on the calculated water content) of methanol. The resulting suspension is stirred at 0° C. for 2 hours and the solid product is collected by filtration, washed with methanol, and dried at 50° C. for 24 hours. HPLC analysis showed that this product is pentostatin contaminated with a 1.1% of the C-8 epimer of pentostatin. This material is recrystallized by dissolving it in 1.2 to 1.5 parts hot (82° C.) water followed by dilution with 10 volumes of methanol with stirring. The resulting mixture is allowed to cool, chilled at 0° C. for 2 hours, and then filtered. The collected solid is washed with methanol and dried at 50° C. in vacuo to give 648.5 g pentostatin of greater than 99.7% purity. This final product is pyrogen free and exhibits ultraviolet, infrared, and NMR spectra that are identical to the corresponding pentostatin spectra reported in *Ann. N.Y. Acad. Sci.* 284: 21–29 (1977).

We claim:

1. A process for isolating pentostatin from a fermentation beer, the process comprising the following steps:

a) applying the fermentation beer to a strong cation exchange resin;

b) eluting the strong cation exchange resin with ammonium hydroxide;

c) concentrating the eluate;

d) adding ethanol and acetone to the concentrated eluate to form a solution;

e) collecting and concentrating the supernatant;

f) applying the concentrated supernatant to a strongly basic anion exchange resin charged with borate ion;

g) eluting the strongly basic anion exchange resin charged with borate ion with water;

h) applying the eluted solution to an activated bed of styrene-divinylbenzene beads prewashed with aqueous ethanol;

i) washing the bed of styrene-divinylbenzene beads with water;

j) eluting the bed of styrene-divinylbenzene beads with ethanol/water;

k) collecting fractions containing pentostatin; and l) recrystallizing the pentostatin using water and methanol to obtain pentostatin having a purity of greater than 99.7%.

2. The process of claim 1 wherein said anion exchange resin of step (f) has a styrene-divinylbenzene polymeric backbone and a trimethylammonium side chain covalently attached.

3. The process of claim 1 wherein said anion exchange resin of step (f) is PUROLITE A-425.

4. The process of claim 1 wherein said styrene-divinylbenzene beads are SEPABEADS SP207.

5. The process of claim 1 wherein the anion exchange resin of step (g) is eluted with seven bed volumes of deionized water.

6. The process of claim 1 wherein the styrene-divinylbenzene beads of step (j) is eluted with 3.5 to 4 bed volumes of ethanol/water.

* * * * *